(12) United States Patent
di Palma

(10) Patent No.: US 7,717,900 B2
(45) Date of Patent: May 18, 2010

(54) LOCKING CLAMP

(75) Inventor: Giorgio di Palma, Queensbury, NY (US)

(73) Assignee: Angio Dynamics, Inc., Queensbury, NY (US)

( * ) Notice: Subject to any disclaimer, the term of this patent is extended or adjusted under 35 U.S.C. 154(b) by 0 days.

(21) Appl. No.: 12/472,827

(22) Filed: May 27, 2009

(65) Prior Publication Data

US 2009/0299338 A1    Dec. 3, 2009

Related U.S. Application Data

(60) Provisional application No. 61/056,553, filed on May 28, 2008.

(51) Int. Cl.
*A61M 25/16* (2006.01)
(52) U.S. Cl. .................................. 604/533; 285/320
(58) Field of Classification Search ............... 604/533, 604/534, 537, 538, 174, 103.03; 285/417, 285/338, 346, 320; 292/DIG. 38
See application file for complete search history.

(56) References Cited

U.S. PATENT DOCUMENTS

| | | | |
|---|---|---|---|
| 3,176,691 A | 4/1965 | Ericson | |
| 3,942,228 A | 3/1976 | Buckman et al. | |
| 4,091,815 A | 5/1978 | Larsen | |
| 4,247,076 A | 1/1981 | Larkin | |
| 4,343,066 A | 8/1982 | Lance | |
| D271,851 S | 12/1983 | Lance | |
| D275,075 S | 8/1984 | Magner | |
| 4,526,172 A | 7/1985 | Stephenson | |
| D283,918 S | 5/1986 | Jacobson | |
| 4,588,160 A | 5/1986 | Flynn et al. | |
| 4,769,004 A | 9/1988 | Poindexter | |
| 4,886,507 A | 12/1989 | Patton | |
| 4,895,340 A | 1/1990 | Forberg | |
| 4,944,485 A | 7/1990 | Daoud et al. | |
| 4,979,703 A | 12/1990 | Fleming | |
| 5,035,399 A | 7/1991 | Rantanen-Lee | |
| 5,083,741 A | 1/1992 | Sancoff | |
| D325,631 S | 4/1992 | Daoud et al. | |
| 5,226,892 A | 7/1993 | Boswell | |
| 5,238,218 A | 8/1993 | Mackal | |
| 5,254,097 A | 10/1993 | Schock et al. | |

(Continued)

FOREIGN PATENT DOCUMENTS

EP    0232233 A1    8/1987

(Continued)

*Primary Examiner*—Melba Bumgarner
(74) *Attorney, Agent, or Firm*—Tara L. Custer

(57) ABSTRACT

A locking clamp is provided that is used for securing at least one tube. The locking clamp has a first and second end axially opposed end pieces and a plurality of locking members extending between the first and second end pieces. Living hinges connect the first and second end pieces to the locking members and allow selective movement of the locking members between an unlocked position and a locked position. In the locked position, the locking members can extend in overlying partially coextensive relation to each other, and the one set of locking members can be defined in a substantially axially opposed, coplanar parallel relationship to the second set of locking members. The clamp may be used during high pressure applications to secure one tube in relationship to another tube.

9 Claims, 4 Drawing Sheets

U.S. PATENT DOCUMENTS

| | | | | |
|---|---|---|---|---|
| 5,338,313 | A * | 8/1994 | Mollenauer et al. | 604/249 |
| 5,428,871 | A | 7/1995 | Iosif | |
| 5,505,714 | A * | 4/1996 | Dassa et al. | 604/534 |
| 5,690,616 | A | 11/1997 | Mogg | |
| 5,855,567 | A | 1/1999 | Reesemann | |
| 5,931,671 | A * | 8/1999 | Hoffman | 433/91 |
| 6,089,527 | A | 7/2000 | Utterberg | |
| 6,708,377 | B2 | 3/2004 | Maunder | |
| 6,712,798 | B2 | 3/2004 | Constantz | |
| 6,780,195 | B2 | 8/2004 | Porat | |
| 7,000,609 | B2 | 2/2006 | Kleen | |
| 7,044,936 | B2 * | 5/2006 | Harding et al. | 604/167.03 |
| 7,062,822 | B2 | 6/2006 | Folkmar | |
| 7,137,611 | B2 | 11/2006 | Aulicino | |
| D593,680 | S | 6/2009 | Hafele et al. | |
| 7,549,200 | B2 | 6/2009 | McMichael et al. | |
| 2005/0035515 | A1 | 2/2005 | Hixon, Jr. et al. | |
| 2006/0270993 | A1 | 11/2006 | McMichael et al. | |
| 2007/0112376 | A1 | 5/2007 | Propp | |
| 2007/0173777 | A1 | 7/2007 | Murphy | |
| 2008/0294122 | A1 | 11/2008 | Chesnin | |

FOREIGN PATENT DOCUMENTS

| | | |
|---|---|---|
| EP | 0241593 A1 | 10/1987 |
| EP | 0276639 A1 | 8/1988 |
| EP | 0350319 A2 | 1/1990 |
| EP | 0799627 A2 | 10/1997 |
| EP | 0718006 B1 | 3/1999 |
| EP | 1698371 B1 | 7/2008 |
| WO | WO2007/112500 A1 | 10/2007 |

* cited by examiner

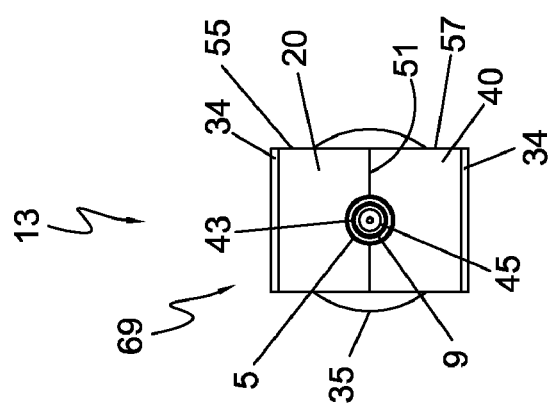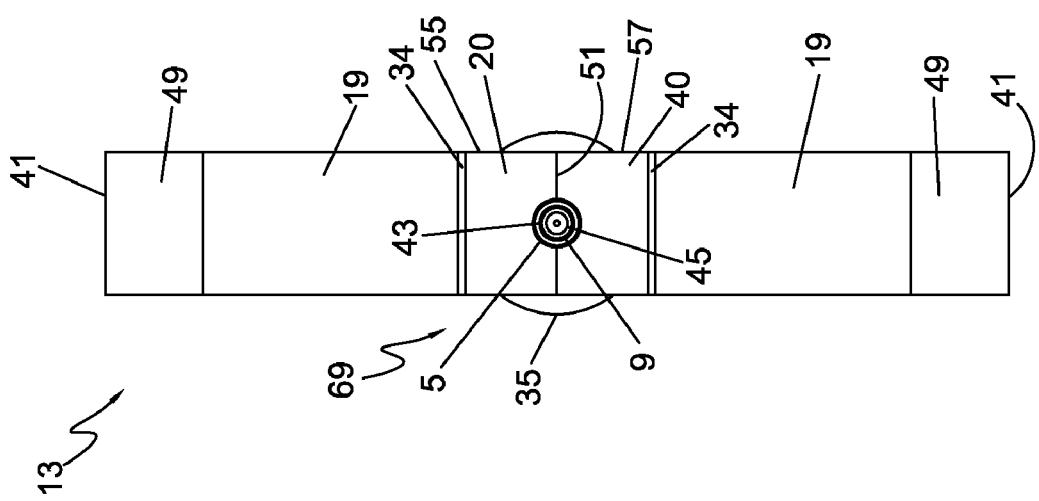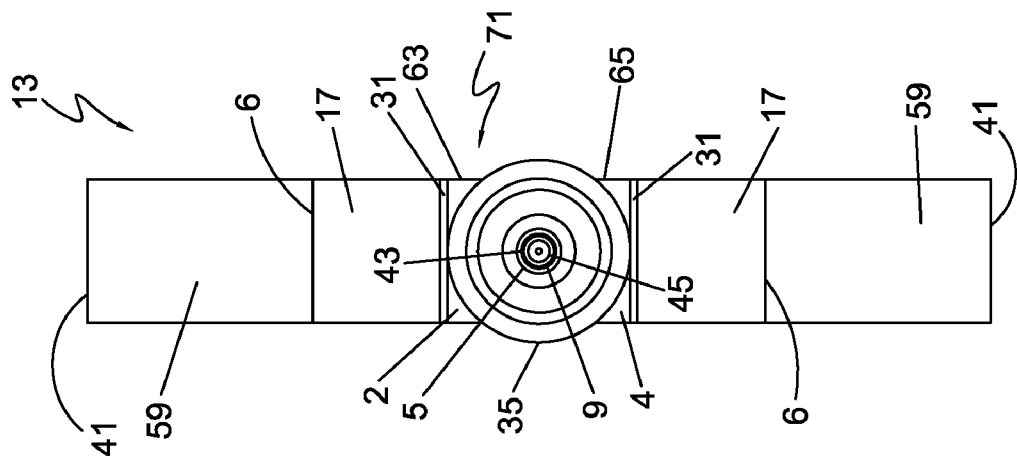

LOCKING CLAMP

This application claims priority to and the benefit of U.S. Provisional Application No. 61/056,553, filed on May 28, 2008, which is incorporated in its entirety in this document by reference.

FIELD OF THE INVENTION

The present invention pertains to the field of medical devices. More particularly, the present invention relates to a locking clamp for use with tubing.

BACKGROUND

Holding a tube stationary inside another tube, such as in a catheter tube, to prevent it from sliding without totally collapsing the fluid path has always been somewhat problematic. One device commonly used in the medical industry to solve this problem has been the use of a Touhy Borst adapter, such as those described in U.S. Pat. Nos. 5,795,307 and 5,320,613. A conventional Touhy Borst adapter is an active valve that is used for attaching catheters to various other devices and has particular utility where a user needs to provide a seal under changing conditions. Touhy Borst valves typically include an O-ring-type element or grommet, usually silicone or rubber, that is seated in a socket forming part of a main passage between an outer wall and a hollow screw mechanism. In operation, a cap threaded on the end of the passage contains a spigot that actively compresses the O-ring or grommet when the cap is selectively rotated to drive the spigot axially inward. The resulting compression closes down the opening in the O-ring around the catheter to prevent "flow-by." When a catheter is absent, the O-ring can be closed down enough to completely close off the opening in the main passage. The compression of the O-ring or grommet in a fixed space does not allow outward expansion and effectively reduces the internal diameter of the O-ring or grommet, which restricts movement of tubing positioned inside the O-ring or grommet.

While conventional Touhy Borst adapters are effective to reduce movement of tubing, the screw mechanism in the Touhy Borst adapter is usually required to be manually turned several times, which is generally a two-handed operation. Touhy-Borst adapters also undesirably require manipulation in order to match the desired diameter of the O-ring or grommet opening to the outside diameter of the catheter. This can be problematic because if a Touhy Borst adapter it is not tightened sufficiently, the valve will leak and blood may flow by the valve. However, if the Touhy Borst adaptor is turned too tight, it may be more difficult to insert the catheter due to friction between the catheter and the grommet or the catheter could be crushed. In addition, the screw mechanism can be over-tightened, which may collapse the tubing being held by the adapter. Further, although Touhy Borst adapters can be used for securing or sealing two tubes relative to each other under low pressures, at higher pressures the adapter needs to be tighter, and more force has to be applied to the tubing with the attendant risk of damage to the tubing being held. Thus, conventional Touhy Borst adapters can be problematic when procedures such as CT injections and sclerotherapy injections are conducted at high pressures, for example, from 200 to 800 PSI.

Other types of valves, such as hemostasis valves, that seal the space between two tubes are well known in the art, but such valves are typically limited to low pressure seals, usually less than 100 PSI. Also, hemostasis valves do not clamp two tubes together, thereby allowing one tube to slide freely within another tube, unless a mechanical device such as a luer lock physically locks them in place. Hemostasis valves do not allow for variable positions, which is required in procedures such as sclerotherapy. In the sclerotherapy procedure, blood vessels are treated by injecting medicine into the vessels, which makes them shrink. This procedure is often used to treat varicose veins. Thus, a device is needed that is capable of functioning under high pressures that can selectively lock a catheter in place and prevent inadvertent disconnections, while allowing variability in position between two tubes, such that they can slide freely in relation to each other.

A device has not yet been proposed that solves all of the above-mentioned problems. A locking clamp that can be used to keep catheter tubing stationary and prevent it from sliding around under high pressures, such as occurs during CT injections or sclerotherapy, is provided herein.

Various other purposes and embodiments of the present invention will become apparent to those skilled in the art as more detailed description is set forth below. Without limiting the scope of the invention, a brief summary of some of the claimed embodiments of the invention is set forth below. Additional details of the summarized embodiments of the invention and/or additional embodiments of the invention may be found in the Detailed Description.

SUMMARY

A locking clamp is provided that is used for securing at least one tube. In one aspect, the locking clamp comprises a first and second end piece that can be positioned in an axially opposed relationship to each other. In another aspect, the locking clamp further comprises a first and a second set of locking members extending between the first and second end pieces. In still another aspect, a plurality of living hinges are integrally coupled to the first and second end pieces and the first and second set of locking members for selective movement of the first and a second set of locking members between an unlocked position and a locked position. In another aspect, an outer elastomeric tube defining an internal lumen can extend between the first and second end pieces. A tube to be secured, such as a catheter tube, can be coaxially aligned therein the lumen of the outer tube. When the plurality of locking members is moved to the locked position, according to another aspect, the tube becomes stretched, making the diameter of the internal lumen of the outer tube smaller. In this aspect, the tube placed inside the internal lumen can be secured in place as the diameter of the lumen decreases.

BRIEF DESCRIPTION OF THE DRAWINGS

These and other features of the preferred embodiments of the invention will become more apparent in the detailed description in which reference is made to the appended drawings wherein:

FIG. 4A is a back end view of the locking clamp in the locked position.

FIG. 4B is a back end view of the locking clamp in the unlocked position.

FIG. 4C is a front end view of the locking clamp in the unlocked position.

DETAILED DESCRIPTION

Figure 1:
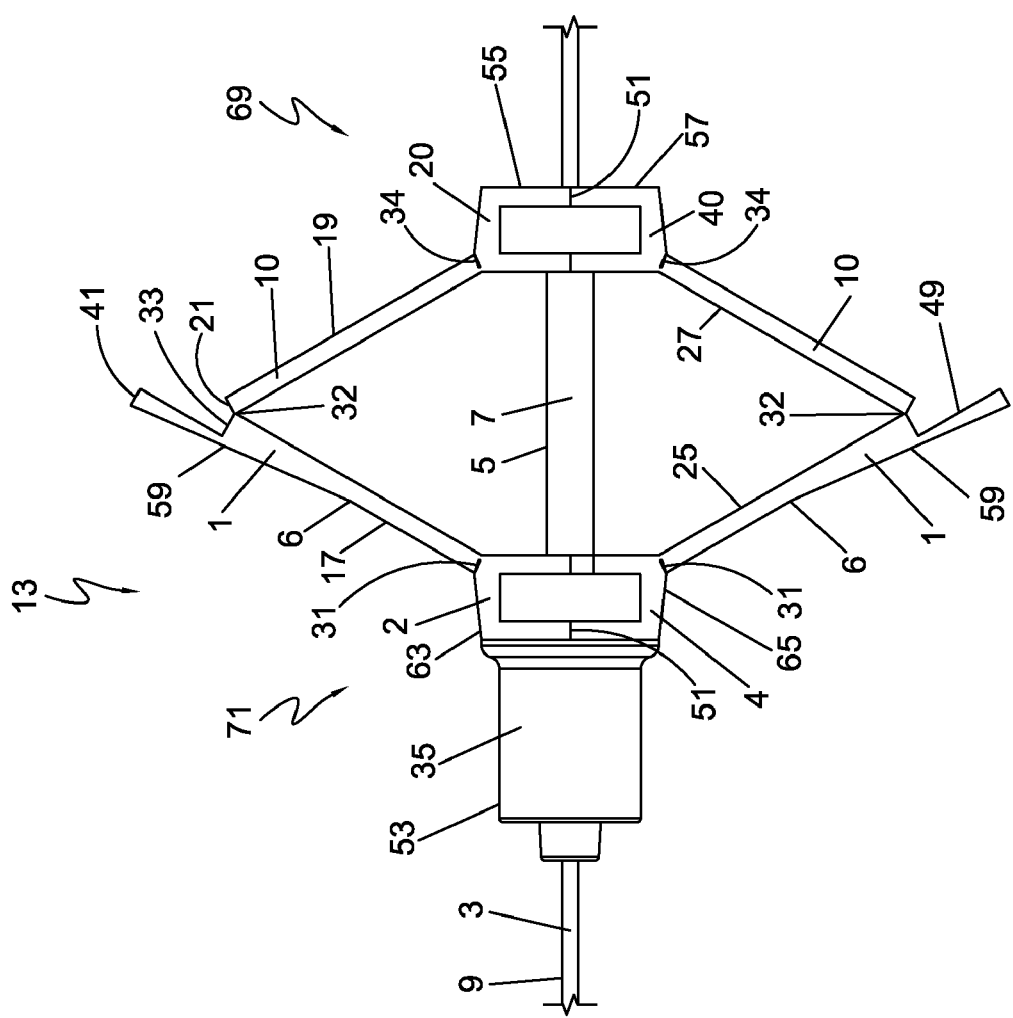
FIG. 1 is a plan view of a locking clamp surrounding a portion of a catheter tube in the unlocked position.

The present invention can be understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a locking member" can include two or more such locking members unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Referring now in detail to the drawings, in which like reference numerals indicate like parts or elements throughout the several views, in various embodiments, and referring to FIGS. 1-4, presented herein is an exemplary locking clamp for use with medical device tubing, such as that used for catheters. In another aspect, the locking clamp described herein may be used with any suitable type of tubing. The locking clamp prevents tubes from becoming disconnected during high pressure applications. In one exemplary aspect, such high pressure applications may include, but are not limited to, CT injections or sclerotherapy.

In one exemplary aspect, FIGS. 1 through 4C illustrate locking clamp 13 described herein. In one aspect, a locking clamp 13 for securing at least one tube in relation to another tube is disclosed. In one aspect, the locking clamp 13 comprises two separate end pieces that are defined in an axially opposed relationship to one another, a first end piece 71 and a second end piece 69. In one exemplary aspect, the first end piece 71 comprises a top portion 2 and a bottom portion 4, and the second end piece 69 comprises a top portion 20 and a bottom portion 40. In another aspect, the top portion 2 of the first end piece can be joined to the bottom portion 4 of the first end piece, and the top portion 20 of the second end piece can be joined to the bottom portion 40 of the second end piece. The top portions 2, 20 and the bottom portions 4, 40 can form a parting line 51 where they are joined together. In another aspect, the top portions 2, 20 may be sealed to the bottom portions 4, 40, respectively, using any suitable adhesive, such as, but not limited to, an epoxy, or any other type of suitable sealant. In other non-limiting examples, the top portions 2, 20 and the bottom portions 4, 40 may be ultrasonically welded together, snap-fit together, or attached to each other by other appropriate methods. In another aspect, the top portion 2 of the first end piece 71 has an outer surface 63, and the bottom portion 4 of the first end piece 71 has an outer surface 65. In another aspect, the top portion 20 of the second end piece 69 has an outer surface 55, and the bottom portion 40 has an outer surface 57. In an assembled state, a portion of the outer surfaces 63, 65 of the first end piece 71 are positioned in axial opposition to a portion of the outer surfaces 55, 57 of the second end piece 69.

The assembled first and second end pieces 69, 71, as illustrated, may have a substantially square shape. Alternatively, any suitable shape may be used for the end pieces 69, 71. In one exemplary aspect, the end pieces 69, 71 may be between approximately 0.25 and 0.75 inches in width. In another aspect, the end pieces 69, 71 may be between approximately 0.3 and 0.5 inches in width. In an exemplary aspect, the width of the end pieces 69, 71 may be approximately 0.5 inches, although any suitable size end piece 69, 71 may be used. The longitudinal depth of the end pieces 69, 71 may be between approximately 0.05 and 0.015 inches. In one exemplary aspect, the depth of the end pieces 69, 71 may be approximately 0.125 inches. In one exemplary aspect, the respective end pieces 69, 71 may be made of any suitable polymeric material, such as, but not limited to, polyurethane, polypropylene, carbothane, Isoplast, polyamide, nylon, polyether block material (PEBA), polyethethersulfone (PES), PP, PE, PCV, ABS resin, or mixtures and copolymers thereof, and the like. One skilled in the art will recognize that other suitable materials may be used for the end pieces 69, 71.

In another aspect, a plurality of living hinges can each be joined along at least a portion of the top portions 2, 20 and the bottom portions 4, 40 of the end pieces 69, 71 at top and bottom corner edges of the outer surfaces 55, 57, 63, 65 of the first and second end pieces, respectively. In one exemplary aspect, two sets of resilient integral living hinges can each comprise a first hinge 31, a second hinge 34, and a third hinge 32. In another aspect, each set of hinges can be coupled to the first and second end pieces 69, 71. In another aspect, a molten thermoplastic polymer can be injected into a cavity of a mold during an injection molding process to produce two molded unitary plastic pieces, a top half and a bottom half, that comprise the living hinges and adjoining polymeric component(s). In one aspect, the top portions 2, 20 of the end pieces can be seamlessly and integrally connected to the first set of living hinges 31, 32, 34, and the bottom portions 4, 40 of the end pieces can be seamlessly and integrally connected to the second set of living hinges 31, 32, 34. In another aspect, the two sets of hinges 31, 32, 34 can be, in turn, seamlessly connected to a plurality of locking members 1, 10. In still another aspect, the locking members 1, 10 can extend from the first and second end pieces towards the opposed respective end piece. In yet another aspect, the plurality of living hinges can be integrally joined to the first and second end pieces and the plurality of locking members for selective movement of the locking members between an unlocked position and a locked position.

Figure 2:
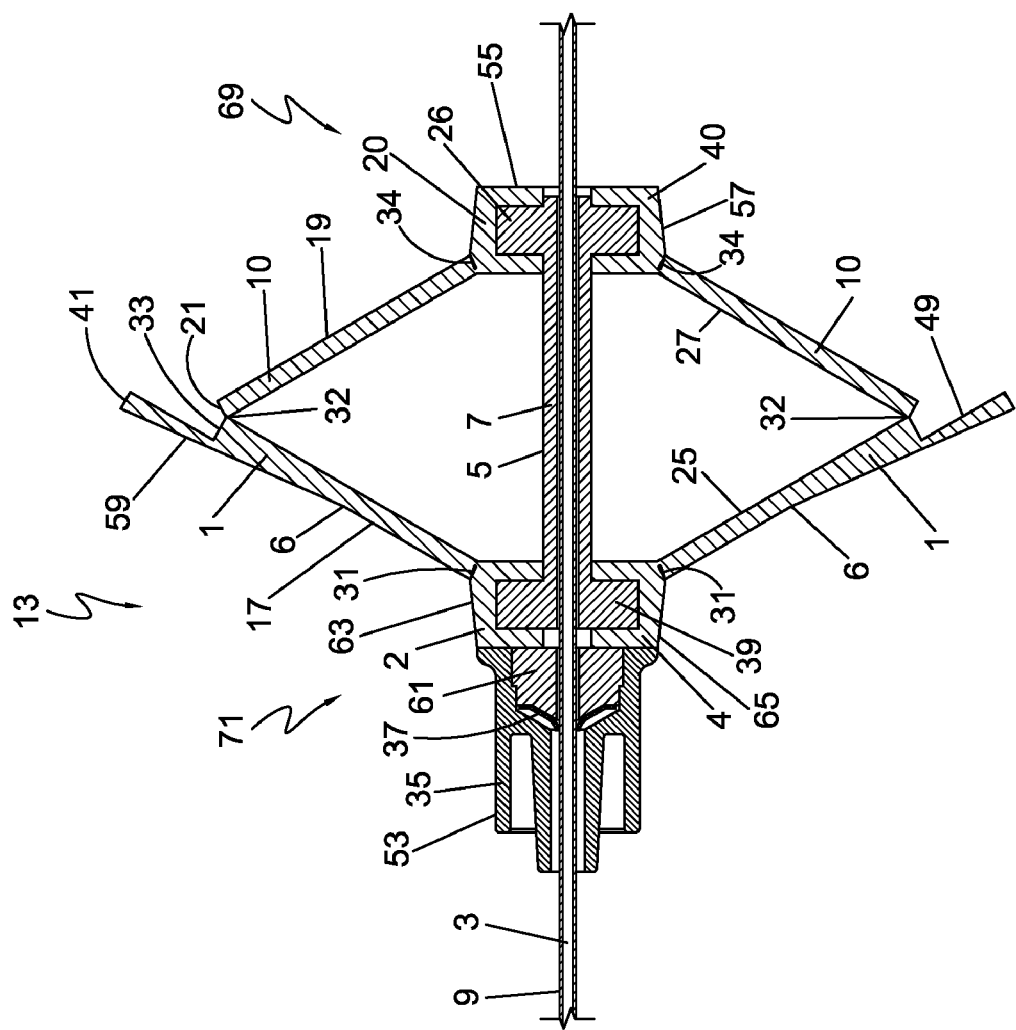
FIG. 2 is a cross-sectional view of the locking clamp of FIG. 1 in the unlocked position.
Figure 3:
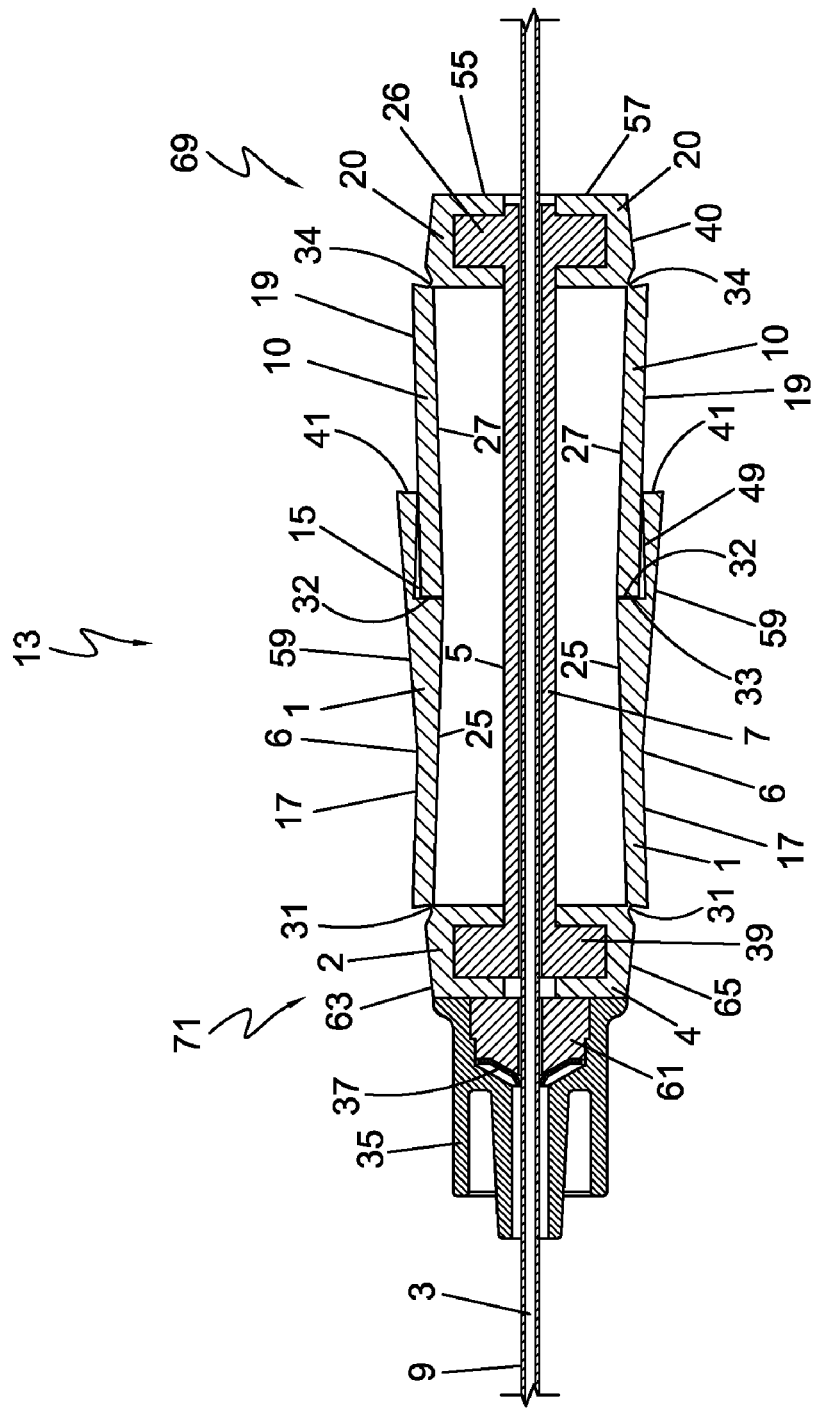
FIG. 3 is a cross-sectional view of the locking clamp of FIGS. 1 and 2 in the locked position.

In one exemplary aspect, the plurality of locking members comprises two sets of locking members wherein each set of locking members comprises a first locking member 1 and a second locking member 10. As illustrated in FIGS. 1-3, the two sets of locking members are mirror images of each other. In another aspect, the plurality of living hinges 31, 32, 34 can be integrally connected to an edge portion of the outer surface 55, 57, 63, 65 of the top portions 2, 20 and the bottom portions 4, 40 of the end pieces, and an edge portion of the locking members 1, 10. In this aspect, the locking members 1, 10 can be selectively and freely moved between an unlocked and a locked position many times without breaking. In another aspect, the first locking member 1 and the second locking member 10 of each set of locking members can be coupled by the third living hinge 32. In one exemplary aspect, the top portions 2, 20 of the end pieces 69. 71 and the first set of living hinges can be injection molded as one single part. Likewise, the bottom portions 4, 40 of the end pieces 69, 71 and the second set of living hinges can be injection molded together as one piece, such that the top half and bottom half form mirror image components of each other. Thus, in this aspect, the injection molding process can produce a molded unitary polymeric top half, comprising the top portions 2, 20 of the end pieces 69, 71, locking members 1, 10, and the first set of hinges 31, 32, and 34. A bottom half, comprising the bottom portions 4, 40 of the end pieces 69, 71, locking members 1, 10, and the second set of hinges 31, 32, 34 can also be produced.

In one aspect, the plurality of living hinges 31, 32, 34 may bend to allow movement of the locking members 1, 10. The living hinges 31, 32, 34, which are known in the art, can be thin, flexible (flex-bearing) hinges that couple two rigid polymeric parts together. In another aspect, the hinges 31, 32, 34 can appear as polymeric components that are seamlessly connected to the end pieces 69, 71 with a crease or score line running through at least a portion of the center of the hinge, along which the living hinge may freely move. The living hinges 31, 32, 34 can be closed and opened over the life of the hinge with little or no loss of function. Living hinges such as these can be desirable because they can be produced at low cost and provide minimal friction or wear. The living hinges are typically made from thermoplastic polymers or plastic, for example, polyethylene, polypropylene, and the like, because these materials have excellent fatigue resistance. In one exemplary aspect, the thermoplastic polymer can be polypropylene.

In one exemplary aspect, the first locking member 1 of the locking clamp 13 has an outer surface that is formed of a first surface 17 and a second surface 59 that are not parallel to each other and which meet at a truncation line 6. The first surface 17 of the outer surface of locking member 1 can be seamlessly connected to the outer surface 63 of the top portion 2 of the first end piece 71 via the first living hinge 31. In another aspect, the first surface 17 of the first locking member 1 extends from a first edge of the first locking member 1 to the truncation line 6, and the second surface 59 of the first locking member extends from the truncation line 6 to an outer edge of the locking member 1. In yet another aspect, the first locking member 1 further has an inner surface 25, a first forward facing surface 41, a second forward facing surface 33, and an under-hanging surface 49. In another aspect, the first forward facing surface 41 and the second forward facing surface 33 can be positioned in a staggered, substantially parallel fashion relative to each other, such that the first forward facing surface 41 is positioned distally from the second forward facing surface 21 to create a shoulder on the first locking member 1. In one exemplary aspect, when the clamp is assembled and in the unlocked position, the first surface 17 and the inner surface 25 of the first locking member 1 can be positioned at an angle of approximately 60 degrees relative to the horizontal plane bisecting the first and second living hinges 31, 34 that connect the first and second locking members 1, 10 to the first and second end pieces 69, 71. In another aspect, the second surface 59 of the first locking member 1 can be positioned at an elevated angle relative to the first surface 17. In one exemplary aspect, the second surface 59 of the first locking member 1 can be positioned at an angle of approximately 70 degrees relative to the horizontal plane bisecting the first and second living hinges 31, 34 that connect the first and second locking members 1, 10.

In one aspect, the second locking member 10 can have an outer surface 19, an inner surface 27 that is substantially parallel to the outer surface, and a forward facing surface 21 that is adjacent the outer and inner surfaces. In another aspect, the second locking member 10 can be coupled to a portion of the outer surface 55 of the top portion 20 of the second piece at a corner edge by the second hinge 34. As illustrated in FIGS. 1 and 2, in one aspect, when the clamp is in the unlocked position, the first locking member 1 and the second locking member 10 can be seamlessly coupled by the third living hinge 32, such that their forward facing surfaces 21, 33 can face outwardly away from the center of the locking clamp 13 and can be slightly angled in toward each other. More particularly, in this aspect, the first and second locking members 1, 10 can be coupled by the third living hinge 32 along a surface edge of the first locking member 1 between the inner surface 25 and the forward facing surface 33, and a surface edge of the second locking member 10 between the inner surface 27 and the forward facing surface 21. In one exemplary aspect, in the unlocked position, the forward facing surfaces 21, 33 can each be positioned at an angle of between about 20 and 30 degrees relative to a plane that is substantially transverse to the longitudinal axis of the clamp. In one aspect, in the unlocked position, the angle between the forward facing surfaces 21, 33 can each be approximately 26 degrees relative to a plane that is substantially transverse to the longitudinal axis of the clamp 13. In one aspect, in the unlocked position, an inner angle formed between the forward facing surfaces 21, 33 can be between approximately 110 to 145 degrees, more particularly between approximately 120 and 135 degrees, and preferably approximately 128 degrees.

In one aspect, after the top half and the bottom half of the locking clamp are formed, as described above, an outer tube 7 comprising a plurality of flanges 39, 26 are disposed at the respective proximal and distal end of the tube 7. In another aspect, the outer tube 7 can have an outer wall 5. In this aspect, each flange 39, 26 of the plurality of flanges can be positioned inside a cavity formed therein the first and second end pieces 69, 71. The top portions 2, 20 and the bottom portions 4, 40 of the end pieces 69, 71 can then be coupled together by molding or sealing the top and bottom portions together along parting line 51 using any suitable adhesive, such as, but not limited to, an epoxy, or any other type of suitable sealant as described above, or any other alternative means such as, but not limited to, ultrasonic welding a snap-fit mechanism, and the like. In one aspect, the top and bottom portions may be sealed using any feasible sealing engagement mechanism that is known in the art and suitable for sealing the top and bottom portions together. In another aspect, the top portions 2, 20 and the bottom portions 4, 40 can be positioned in surrounding relationship to flanges 39, 26 of the outer tube 7. In yet another aspect, a catheter tube 3 having an outer wall 9 and an inner wall 45 may be positioned within the outer tube 7.

In one aspect, the outer tube 7 can extend longitudinally between and be secured by the end pieces 69, 71 once the top and bottom portions 2, 4 of the first end piece 71 and the top and bottom portions 20, 40 of the second end piece 69 have been coupled. In another aspect, the top portion 2 and the bottom portion 4 of the first end piece 71 can surround a first flange 39 of the plurality of flanges of the outer tube 7. In still another aspect, the top portion 20 and the bottom portion 40 of the second end piece 69 can surround a second flange 26 of the outer tube 7.

In one aspect, the outer tube 7 may be made of any suitable elastomeric material, such as, but not limited to, rubber (e.g., natural rubber, silicone rubber, nitrile rubber, or polysulfide rubber) and the like to allow the elastomeric tube to be easily stretched. In one aspect, the outer tube 7 may have an outer diameter of between about 0.10 and 1.0 inches, and an inner diameter of between about 0.01 and 0.9 inches. In an exemplary aspect, the outer tube 7 may have an outer diameter of approximately 0.131 inches and in inner diameter of approximately 0.067 to 0.070 inches. In another aspect, the outer tube can have an inner wall 43 defining an inner diameter sized such that a desired catheter tube may fit therein a lumen of the outer tube 7.

In one aspect, the catheter tube 3 may be composed of, but is not limited to, carbothane, silicone, polyurethane, polyethylene, Teflon, and the like, or any suitable polymeric material. In one aspect, the catheter tube 3 may have an outer diameter between about 0.01 and 0.9 inches. In one exemplary aspect, the catheter tube 3 may have an outer diameter of approximately 0.066 inches (a 5 Fr inner catheter tube). As one skilled in the art will appreciate, other diameter catheters are contemplated. In one aspect, and as illustrated in FIGS. 1 through 3, in both the unlocked and the locked positions, the catheter tube 3 can be inserted into the outer tube 7 such that the outer tube, the first end piece 69 and the second end piece 71 surround at least a portion of the outer wall 9 of the catheter tube 3. FIG. 2 illustrates a cross-section of the locking clamp 13 in surrounding relationship to the outer tube 7, which surrounds inner catheter tube 3.

In one aspect, a luer lock 35 comprising a secondary valve 37 and having an outer wall 53 can be positioned adjacent to the first end piece 71 of the locking clamp 13. In one aspect, the outer wall 53 of the luer lock 35 may be secured to the front end piece 71 using any reasonable sealing mechanism, such as, but not limited to, an epoxy, or any other type of sealant and the like. In another aspect, the secondary valve 37 can be positioned inside of the luer lock 35. In one aspect, the valve 37 can be in the form of a thin membrane having a circular shape and a hole defined in the center of the membrane through which the outer tube 7 and catheter tube 3 may be inserted. In another aspect, this valve 37 can function as a seal and can bend in only one direction when pressure is applied to the catheter tube 3 or the outer tube 7, which can be inserted through the luer lock. In one aspect, as fluid pressure builds up from the catheter tube 3 to the luer lock 35, the valve 37 forms a seal. As the valve forms a seal, the valve 37 moves axially towards the first end piece 71. In another aspect, because the valve 37 works on differential pressure, the higher the pressure in a space between the outer tube 7 and the catheter tube 3, the better the valve 37 will seal.

In another aspect, the luer lock 35 can further comprise a seal backing 61 that is positioned between the first end piece 71 and the valve 37. In one aspect, the seal backing 61 helps to receive some of the pressure that builds up on the valve 37 as the valve 37 moves axially towards the first end piece 71 and presses upon the seal backing 61. In use, as pressure builds up inside the catheter tube 3, the pressure travels through the catheter tube 3 toward the luer lock 35 and is prevented from progressing further when the pressure reaches the seal backing 61. Thus, in this aspect, the seal backing 61 can also serve as a stop measure for preventing further movement of the valve 37. This can prevent pressure from backing up into the outer tube 7 or the catheter tube 3.

In the locked position, in one aspect and as illustrated in FIG. 3, the first set of locking members and the second set of locking members can extend in overlying partially coextensive relation to each other. In another aspect, it is contemplated that one set of locking members can be positioned in substantially an axially opposed, coplanar parallel relationship to the second set of locking members. In one exemplary aspect, the first set of locking members and the second set of locking members are defined in parallel relation to a horizontal plane bisecting the first and second end pieces of the clamp 13. More particularly, the inner surfaces 25, 27 of the first and second locking members 1, 10 can be defined in an opposed, substantially parallel direction to the outer wall 5 of tube 7.

Optionally, in another aspect and as illustrated in FIG. 3, in the locked position, the inner surfaces 25, 27 of the first and second locking members 1, 10 can be positioned at a slight, inwardly directed angle in relation to a horizontal plane bisecting the corners of the living hinges 31, 34. In one exemplary aspect, the first locking member 1 and the second locking member 10 of the first and second sets of locking members may be positioned at an angle of approximately 0.5 to 10 degrees relative to a horizontal plane bisecting the corners of the living hinges 31, 34, more particularly at an angle of approximately 1 to 5 degrees, and most preferably at an angle of approximately 2 degrees. Thus, in this exemplary aspect, the living hinge 32 is positioned closer to the longitudinal axis of the clamp 13 than the respective living hinges 31, 34.

In one aspect, when in the locked position, the angled positions of the first and second locking members 1, 10 can enable the locking clamp 13 to selectively lock into position, thereby making it more difficult to inadvertently unlock the locking members 1, 10 from the locked position. In contrast, if the locking members 1, 10 formed a straight line positioned parallel to the longitudinal axis of the clamp, it would be easier to unlock the locking members because less force would have to be applied to cause the locking members 1, 10 to return to their original unlocked position. In one aspect, the second forward facing surface 33 of the first locking member can abut up against the forward facing surface 21 of the second locking member 10 when the locking members 1, 10 are joined together in the locked position, as illustrated in FIG. 3. In another aspect, when the clamp and the locking members are in the locked position, the forward facing surfaces 21, 33 can be positioned substantially parallel relative to each other. In another aspect, in the locked position, the under-hanging surface 49 can be positioned in a substantially parallel position to the longitudinal axis of the clamp 13. In the locked position, the outer surfaces 63, 65 of the first end piece 71 and the outer surfaces 55, 57 of the second end piece 69 can each form a substantially ninety degree angle with respect to the outer edges of the first and second locking members 1, 10.

In one aspect, when the locking members 1, 10 are positioned in the locked position, as illustrated in FIG. 3, the combined length of the first and second locking members 1, 10 may be approximately 0.7 inches to 1.5 inches. In another aspect, the locking members 1, 10 can be approximately 1 inch in length in the locked position. In another aspect, the width of the first and second locking members 1, 10 may be approximately 0.8 to 1 inches.

FIG. 3 illustrates the locking clamp 13 in a locked position. In one aspect, in the locked position, the inner surfaces 25, 27 of the first set of locking members of the locking clamp 13 can be positioned in an axially opposed position relative to the inner surfaces 25, 27 of the second set of locking members of the locking clamp. In another aspect, in the locked position, a small cavity 15 can be defined between the under-hanging surface 49 of the first locking member 1, the second forward facing surface 33 of the first locking member 1, and the outer surface 19 of the second locking member 10. In another aspect, when the locking members 1, 10 are moved from the unlocked position to the locked position, the plurality of living hinges 31, 32, 34 can transition from a stressed position to a non-stressed position.

When the locking members 1, 10 and thus, the locking clamp 13 are moved from the unlocked to the locked position, according to one aspect, the respective end pieces 69, 71 are axially moved apart, which stretches the outer tube 7 and effectively reduces the internal diameter of the outer tube. In this aspect, as the inner diameter of the outer tube becomes smaller, an inner wall 43 of the outer tube 7 can have more frictional contact with the outer wall 9 of the catheter tube 3. Friction between the outer tube 7 and the catheter tube 3 being positioned within the outer tube 7 helps to keep the catheter tube 3 selectively locked into a desired position. In another aspect, because the stretching of the outer tube 7 is limited by the size of the locking clamp 13, the reduction of the internal diameter the outer tube is limited, which prevents the possibility of distortion or collapse of the outer tube. Alternatively, in one exemplary aspect, the internal diameter of the outer tube 7 may be decreased by manually twisting or causing the outer tube 7 to be twisted.

FIG. 4A illustrates a back end view of the locking clamp 13 in the locked position, according to one aspect. In the back end view, the second living hinges 34 are visible along a surface edge of the second end piece 69. In another aspect, the second living hinge 34 spans the width of the top portion 20 and the bottom portion 40 of the second end piece 69. In another aspect, the parting line 51 divides the outer surface 55 of the top portion 20 of the second end piece and the outer surface 57 of the bottom portion 40 of the second end piece 69. Still with reference to FIG. 4A, a partial view of the luer lock 35 is visible on either side of the second end piece 69. From the back end view of the locking clamp 13, the coaxial relationship of the outer tube 7 and the inner catheter tube 3 can be seen, according to one aspect. Additionally, the outer tube 7 is in a surrounding relationship to the catheter tube 3.

FIG. 4B illustrates a back end view of the locking clamp 13 in the unlocked position, according to one aspect. In the back end view, the second living hinges 34 are opened, such that they are in a stressed state. As seen in the back end view of the unlocked position, the top surface 41 of the first locking member faces generally away from the longitudinal axis of the clamp 13. Still with reference to FIG. 4B, the under-hanging surface 49 of the first locking member 1 is visible, and the outer surface 19 of the second locking member 10 is positioned adjacent to surface 49.

FIG. 4C illustrates a front end view of the locking clamp 13 in the unlocked position, according to one aspect. In the front end view, the outer circular profile of the luer lock 35 is visible and extends beyond the sides of the outer surface 63, 65 of the first end piece 71. In this aspect, the outer surface 53 of the luer lock 35 surrounds the outer wall 5 of the outer tube 7, which in turn, surrounds the catheter tube 3 that is positioned inside of the outer tube 7 and the coaxial relationship between the outer tube 7 and the catheter tube 3 can be seen. The first surface 17 and the second surface 59 of the outer surface of the locking member are divided by truncation line 6 that is visible from the front end.

In use, the locking clamp 13 allows for the prevention of the inadvertent disconnection of the catheter to a hub or of a hub to a check valve connection. With conventional locking mechanisms, it has been observed during bench testing that if the luer connections are sufficiently tightened, catheter tubing can disconnect during the high pressure injections, such as occurs during CT injections or sclerotherapy, resulting in sclerosant or other fluids to spray from the connections. The locking clamp 13 described herein, however, functions to prevent this disconnection. In addition, the locking clamp 13 can be closed with a single hand, which is beneficial for medical practitioners.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the appended claims. Moreover, although specific terms are employed herein, as well as in the claims which follow, they are used only in a generic and descriptive sense, and not for the purposes of limiting the described invention, nor the claims which follow.

What is claimed is:

1. A clamp for securing at least one tube, comprising:
a first end piece and a second end piece, wherein each end piece has a top portion and a bottom portion, and wherein the first and second end pieces are positioned in axially opposed relationship to each other;
a first set of locking members comprising a first locking member rotatably coupled to and extending from the top portion of the first end piece and a second locking member rotatably coupled to and extending from the top portion of the second end piece;
a second set of locking members comprising a first locking member rotatably coupled to and extending from the bottom portion of the first end piece and a second locking member rotatably coupled to and extending from the bottom portion of the second end piece;
a first means for rotatably coupling the first locking member and the second locking member of the first set of locking members;
a second means for rotatably coupling the first locking member and the second locking member of the second set of locking members;
an outer tube mounted to and extending therebetween the respective first and second end pieces;
wherein, the first and second sets of locking members are configured for selective axial movement between a locked position, in which the respective first and second end pieces are positioned axially apart at a maximum distance, and an unlocked position, in which the respective first and second end pieces are positioned axially apart at a distance less than the maximum distance, and wherein, in the locked position, the outer tube has an inner diameter that is less than the inner diameter of the outer tube in the unlocked position.

2. The clamp of claim 1, wherein the outer tube is an elastomeric tube.

3. The clamp of claim 1, further comprising a luer lock adjacent the first end piece.

4. The clamp of claim 1, wherein the first means for rotatably coupling the first locking member and the second locking member of the first set of locking members comprises a living hinge.

5. The clamp of claim 1, wherein the second means for rotatably coupling the first locking member and the second locking member of the second set of locking members comprises a living hinge.

6. The clamp of claim 1, wherein the at least one tube comprises a catheter tube.

7. The clamp of claim 1, wherein, in the unlocked position, the first locking member and the second locking member of the first set of locking members are positioned at an acute angle relative to each other.

8. The clamp of claim 1, wherein, in the locked position, a forward facing surface of the first locking member of the first set of locking members and a forward facing surface of the second locking member of the first set of locking members are adjacent and substantially parallel to each other.

9. A clamp for securing at least one tube, comprising:
a first end piece and a second end piece, wherein the first and second end pieces are positioned in axially opposed relationship to each other;
a pair of opposed first locking members hingeably coupled to and extending from the first end piece;
a pair of opposed second locking members hingeably coupled to and extending from the second end piece, wherein first locking members are hingeably coupled to respective second locking members, and wherein the respective first and second locking members are moveable about and between a locked position, in which the respective first and second end pieces are positioned axially apart at a maximum distance, and an unlocked position, in which the respective first and second end pieces are positioned axially apart at a distance less than the maximum distance.
an outer tube mounted to and extending therebetween the respective first and second end pieces, wherein, in the locked position, the outer tube has an inner diameter that is less than the inner diameter of the outer tube in the unlocked position.

\* \* \* \* \*